United States Patent [19]

Hartmann et al.

[11] 4,126,396
[45] Nov. 21, 1978

[54] DEVICE FOR THE NON-DISPERSIVE OPTICAL DETERMINATION OF THE CONCENTRATION OF GAS AND SMOKE COMPONENTS

[75] Inventors: Klaus Hartmann, Munich; Meinhard von Braitenberg, Grunwald, both of Fed. Rep. of Germany

[73] Assignee: Erwin Sick Gesellschaft mit Beschrankter Haftung, Optik-Elektronic, Waldkirch, Fed. Rep. of Germany

[21] Appl. No.: 685,425

[22] Filed: May 11, 1976

[30] Foreign Application Priority Data

May 16, 1975 [DE] Fed. Rep. of Germany ....... 2521934

[51] Int. Cl.$^2$ .................................................. G01N 21/26
[52] U.S. Cl. ................................... 356/434; 250/373; 250/573; 356/51; 356/438
[58] Field of Search ................. 356/51, 188, 189, 201, 356/205–207; 250/343, 373, 573, 574, 576

[56] References Cited

U.S. PATENT DOCUMENTS

| 3,472,594 | 10/1969 | Hughes et al. | 356/205 X |
| 3,796,887 | 3/1974 | Vincent et al. | 250/373 X |
| 3,857,641 | 12/1974 | Gass | 356/207 |
| 3,860,818 | 1/1975 | Stalder et al. | 356/51 X |
| 3,885,162 | 5/1975 | Geertz | 356/207 X |

FOREIGN PATENT DOCUMENTS

2,142,525  1/1973  France .................................... 356/201

Primary Examiner—F. L. Evans

[57] ABSTRACT

A method and apparatus for non-dispersive optical determination of gas and smoke components in a mixture by reflection and detection of radiation, of a different wavelength for each component, through the mixture, wherein the radiation is periodically intercepted before it enters the mixture and reflected direct to the photo-receiver and the measurement signals are divided by the stored direct signals.

29 Claims, 8 Drawing Figures

DEVICE FOR THE NON-DISPERSIVE OPTICAL DETERMINATION OF THE CONCENTRATION OF GAS AND SMOKE COMPONENTS

The invention relates to a method for the non-dispersive optical determination of the concentration of gas and smoke components in a mixture of various gases and possibly smoke, in which radiation of at least as many different wavelengths as there are gas components and possibly a smoke component in the mixture to be measured, is conducted through the mixture, reflected, conducted through the mixture again and picked up at successive times periodically by a photoreceiver, from whose output signals, representing the particular transmission concerned, the concentrations of the components are computed by Beer's Law.

The basis for each concentration measurement on the principle of radiation absorption is Beer's Law, according to which the transmission of an irradiated sample depends exponentially on the product of the measured length L and the sample concentration c in accordance with the following formula:

$$T = I(\lambda)/I_o(\lambda) = \exp.[-k(\lambda) \times L \times c] \quad (1)$$

Here $I_o(\lambda)$ and $I(\lambda)$ are radiation intensities of a given wavelength at the beginning and end, respectively, of the absorption length. $k(\lambda)$ is the wavelength-dependent absorption coefficient of the examined gas component and it often happens that a number of gas components absorb differently at the same point of the spectrum, this being manifest as the so-called cross-sensitivity in the measurement.

Since measurement of radiation intensities is generally carried out with one radiation detector the measurement is falsified not only by variations in the radiation intensity of the source of radiation and radiation losses in the optical path but also by changes in the sensitivity of the radiation detector. The continuous variations in the measured radiation intensities, independently of absorption losses in the measurement length, are also designated as the drift of the arrangement.

The known non-dispersive gas analysers can be divided, irrespective of the spectral range employed, into two groups, that is to say equipment utilising optical filter arrangements or selective radiation sources for wavelength selection and equipment effecting spectral separation by way of gas-filled vessels.

To obviate the so-called cross-sensitivity (by this is to be understood the influencing of absorption at a certain point on the spectrum by a different gas which likewise absorbs at this point) with equipment of the second type, the work is carried out with a dual beam arrangement, wherein radiation emanating from one or two sources passes through spatially separated measuring and comparing vessels which are charged with the gas sample to be examined, and a neutral gas, respectively. The different radiation absorption in the two vessels is measured in radiation detectors specially constructed according to the spectral range for producing electric signals. There are also single beam arrangements in which a single vessel is filled alternatively with test gas and with reference gas, but this is very complicated.

A detailed account of this type of gas analyser can be found in the article "Neuester Stand der Entwicklung von Kontrollmessgeräten zur Dauerüberwachung von Gas-Emissionen" ("Latest state of development of monitoring and measuring apparatus for the continuous monitoring of gas emissions") by H. W. Thoenes and W. Gruse, which appeared in the periodical "Staub-Reinhaltung der Luft" (Maintenance of dust-free air), 28 (1968), Pt. 3, pp. 128–134.

In their use for continuous monitoring of emission these equipments have the main disadvantage of requiring a system for the removal and the preparation of the test gas. Apart from the complexity of this method, errors may occur in gas removal so that the partial flow obtained for measurement is no longer representative of the waste gas. Disturbing foreign substances, such as solid particles, water vapour and aerosols must be removed from the flow of measurement gas so that the withdrawal and cleaning system with its connecting lines does not become clogged or corroded. The filters, coolers and receivers used in preparation of the test gas must not affect or adulterate the components being measured.

In a further known arrangement (DT-OS 2,324,049) which seeks to obviate these difficulties by direct measurement in the duct carrying the waste gas, for example a stack, the radiation source, optical filter unit, detector and electronic evaluating system are brought together in a housing outside the stack, while projecting into the stack from the side is a gas-permeable probe at the end of which the radiation is deflected by a mirror and thus arrives back in the measuring head. Measuring is carried out in the ultraviolet portion of the spectrum by the combination of two wavelengths respectively for the gas components $SO_2$ and $NO_2$ as well as electronic evaluation of the two transmission values to determine the gas concentration. For balancing and for the regular obtaining of a neutral and calibration point the probe is cleansed with a neutral gas which does not contain the components being measured.

In another known arrangement (DT-OS 2,340,747) the radiation source and also the detector and evaluation unit are mounted opposite one another in separate housings on the stack and interconnected by way of a gas-permeable pipe. The radiation source consists of two hollow cathodes of different emission wavelengths, tuned to the ultraviolet $SO_2$ absorption band, the intensity of which is measured and evaluated in the detector unit after the passage through the stack. A second photodetector is provided in the transmission part to pick up any changes in the radiating capacity, which may occur in the two hollow cathode lamps.

There is also a report on dispersive and non-dispersive radiation analysers measuring directly in the waste gas stack in an article entitled "Monitoring Boiler Stack Gases" by T. C. Elliott in the periodical "Power" (April 1975), pp. 92–94.

A separate arrangement of transmitter and receiver unit on the stack is highly sensitive to adjustments, just like deflection of rays within a probe by means of a mirror, and so the intensity of radiation passing over the measured distance depends substantially on the geometrical orientation and stability of the arrangement on the stack. Of course it remains possible to measure the gas content by the two-wavelength method so long as both radiation components follow the same optical path in what is always the same mixture in space. On the other hand it is scarcely possible to measure the proportion of smoke in the waste gas with arrangements of this type because solid particles other than a gas component reduce the transmissivity for both wavelengths and therefore require the unattenuated radiation as a reference.

Every variation in radiation intensity which is due to adjustment would appear as a measuring error in the determination of the solid content. Moreover cross-sensitivity to other gas components cannot be excluded even with the two-wavelength method; it exists over wide ranges of the infra red spectrum through the absorption bands of water vapour and must also be taken into consideration in the ultraviolet range owing to the wide nitrogen dioxide bands.

The equipments measuring directly in the stack according to the present state of the art allow for no special arrangements or measures to compensate for the aforementioned cross-sensitivity. For continuous monitoring of emissions long-term stability is also an important requirement of the equipment which can only be satisfied with great difficulty when operating with a plurality of beam transmitters or receivers. Again, the formation of quotients in measuring with two wavelengths compensates drift effects in the optical and electro-optical components only in so far as they are not dependent on wavelength. Finally, the known method with direct measurement in the waste gas stack has the disadvantage that the probe which is introduced covers only a part of the cross-section of the stack which need not necessarily be representative of the total flow of waste gas.

The aim of the invention is therefore to create a method and a device of the type referred to above which will obviate the aforementioned disadvantages of the known equipment and permit a substantially more accurate measurement of concentration by means of radiation absorption, while eliminating in particular the disadvantages of the spectrally different drift effects.

As a solution of this problem the invention provides that, at predetermined intervals of time and for at least one period of reception, the beams shall, even before entering the mixture, be reflected over the same beam path direct to the photo-receiver and the electric reference signals obtained for the various test wavelengths shall be stored during the successive predetermined interval of time and that the output signals representing the respective transmission shall, before computation of the concentrations, be divided by the stored reference signal obtained with the same wavelength. The idea underlying the invention is, thus, the compensation of the wavelength-dependent influences of the spectral sensitivity of the photo-receiver and of the spectral emissivity of the source of radiation as well as any other influences of the optical components. Thus the drift effects are completely eliminated by the method according to the invention and, indeed, even when they are dependent on wavelength. Only the two reflectors must be stable and controlled with exclusion of gas absorption.

In general it is sufficient if the reference signals are formed anew and stored every 10 minutes because in shorter intervals the drift effects are practically unnoticeable. In principle even longer intervals would be adequate for the formation of the reference signals. With the electronic holding circuits at present employed in analogue techniques the 10-minute cycle is preferred; with digital circuitry it is possible to choose longer intervals.

It is particularly advantageous if both the measuring and the reference signals can be regulated to the same level for the same basic conditions. This can be achieved, for example, by different amplification of the individual signals and it leads to particularly simple computational evaluation.

Where the mixture consists of smoke, $SO_2$ and $NO_2$ the measurement wavelengths are conveniently 313, 435 and 546 nm, since the associated absorption coefficients of the said components yield transmission signals which can be evaluated well for the concentrations generally present in waste gas stacks and where there is complete radiation of the stack.

The invention also has as its subject a particularly convenient device for carrying out the aforementioned method with a light transmitter-receiver for the beams disposed at one end of the measurement distance and a reflector at the other end of the measurement distance, also a computing circuit to determine the concentrations from the electric signals formed by the light receiver, characterized in that, before entering the measured distance, the beam of light coming from the light transmitter-receiver can be brought optionally on to a reference reflector which reflects the beam in the same direction as the reflector disposed at the end of the measured distance. As a result of this arrangement the reference signals needed for drift compensation can easily be formed between the test periods by projecting the beam of light on to the reference reflector.

It is convenient if the reference reflector can be swung into the path of the beam between the light transmitter-receiver and the measured distance. In a practically advantageous form of construction the reference reflector is fixed to a lever arm articulated immediately beside the front objective of the light transmitter-receiver, and an actuating rod is articulated preferably at a relatively short distance from the pivot of the lever arm and can be driven by a motor through a crank in one direction or the other. In this way, with relatively small movements, big excursions of the lever arm carrying the reference reflector can be obtained, thus permitting a rapid swing-in which is, however, controlled and free from violent impact.

The reflectors are preferably retroreflectors, especially triple mirrors, and the one disposed at the end of the measured distance, at least, should be radiated all round by the light beam.

This form of construction is particularly convenient when the light transmitter-receiver and the retro-reflector are disposed on opposite sides of the stack, when as is known, varied expansions of the stack walls due to heating may result in considerable distortion. However, as a result of the construction according to the invention with radiation over the retroreflector these distortions have no adverse effect on the measurement.

A particularly simple optical arrangement together with good insensitiveness to adjustment is obtained by using an autocollimation beam path.

For measuring a smoke component, an $SO_2$ component and an $NO_2$ component a low-pressure mercury-vapour lamp is especially suitable because it has emission bands at the measuring wavelengths 313, 435 and 546 nm.

Selection of wavelength is effected conveniently by a filter wheel which has on a first circumference filters which arrive in succession in the reception beam path. In measurements of smoke, $SO_2$ and $NO_2$ and also when a low-pressure mercury-vapour lamp is being used it is then sufficient to construct the filters of combinations of tinted glass which, as is known, are relatively wide banded. However, in view of the emission characteristic of the low-pressure mercury lamp wide-band filters of this type are sufficient.

It is also convenient to provide a dark zone also in the filter sequence to define the neutral point in the electronic evaluation.

There are further provided preferably on a second circumference of the filter wheel control slots co-operating with a light barrier and a master clock, each of which is associated with a filter or the dark zone. Here, the master clock effects the blanking of the particular wavelength signal which is just formed at a certain moment.

Finally, on a third circumference there is provided a control aperture co-operating with a light barrier and the master clock, by means of which the re-setting of the master clock and hence an indication of the start of the respective cycle is obtained.

The photo-receiver is advantageously connected by way of a pre-amplifier to a channel balancing stage which has two balancing amplifiers for each measuring wavelength. With suitable balancing by the amplifiers it is possible, in the absence of smoke and test gas, to boost all the test and reference signal levels to the same value, which is advantageous to later evaluation.

In a further suitable arrangement the channel balancing stage is so constructed, utilising a certain operating range of the computing circuit, to be described hereinafter, that, economising on balancing amplifiers, only a paired coincidence of measuring and reference signal levels is adjusted in the absence of smoke and test gas for one test wavelength at a time, whereby optimally, with additional optical fine balancing for one wavelength with the aid of the iris diaphragm at the above-described reflectors, only two balancing amplifiers are needed for the channel balancing stage.

It is preferable if a balancing amplifier is also provided for the dark zone in the channel balancing stage.

In a further advantageous form of construction an electronic switch controlled by the master clock is connected to the channel balancing stage and stored the wavelength, test and reference signals and, where applicable, also the dark zone signal individually in holding circuits.

Then the computing circuit is connected to the switch and interrogates in pairs the measurement and reference signals associated with the same wavelength and divides one by the other. This division represents the critical step according to the invention because all parameters impairing the measurement through drift effects hereby drop out.

To arrive at the concentration data, logarithms are taken appropriately in the computing circuit of the signals which have been divided one by the other.

The logarithm signals representing the extinctions are preferably stored in holding circuits.

Finally there is a computing stage connected to the holding circuits which from the logarithm signals forms the concentration signals which can be displayed on any kind of indicating instrument.

The invention is described below by way of example with reference to the drawing in which the Figures are as follows.

Figure 1:
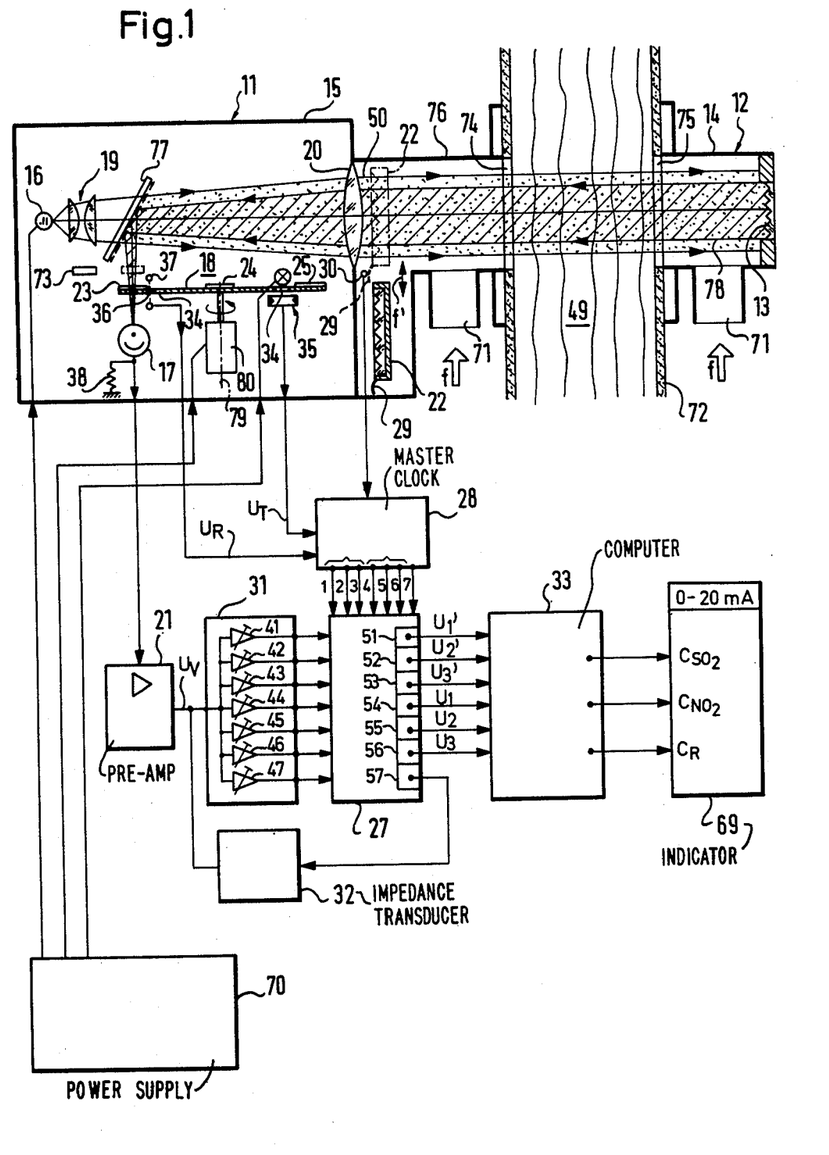
FIG. 1 is a diagram of a preferred device and circuit for carrying out the method of the invention.

As shown in FIG. 1 the device according to the invention has a light transmitter-receiver 11 fixed to one side of a stack 72 and a reflector head 12 fixed to the opposite side of the stack 72 and consisting of a housing 14 and a retro-reflector 13 disposed on its end face. The stack 72 has apertures 74, 75 for the passage of the light beam in the region of the light transmitter-receiver 11 and the reflector head 12.

The housing 14 of the reflector head 11 and a connecting branch 76 which connects the housing 15 of the light transmitter-receiver 11 to the stack 72 are provided with supply pipes for scavenging air 71 through which scavenging air is blown in, in the direction of the arrow f, to prevent impurities getting from the stack 72 into the connecting branch 76 or the front objective 20 and becoming deposited there.

Fitted in the housing 15 of the light transmitter-receiver is a radiation source 16, preferably constituted by a low-pressure mercury-vapour lamp, which by way of a condensing lens 19 and a beam-splitting mirror 77 fully illuminates a front objective 20 disposed in the end wall of the housing 15. From the front objective 20 there emerges an almost parallel and preferably slightly divergent beam of light 50 which traverses the connecting branch 76, the stack 72 permeated by flue gases 49 and finally the housing 14 of the reflector head 13 to impinge on the retroreflector 13 which preferably consists of triple mirrors. It is important that at the site of the reflector 13 the light beam 50 is of a greater diameter than the retroreflector so as to give all-round irradiation of the reflector 13 as can be seen from FIG. 1. In this way the flow of light thrown back from the reflector 13 undergoes no change in the event of certain relative shifts or tiltings of the optical axis between the reflector head 12 and the light transmitter-receiver.

Owing to the ratio of dimensions of the light beam 50 and the retroreflector 13, the reflected beam 78 has a smaller diameter than the beam 50 — likewise almost parallel — which leaves the transmitter.

The reflected beam 78 is concentrated, by the objective 20 and after reflection at the beam-splitting mirror 77, on a photo-receiver 17 in front of which is disposed, according to the invention, a filter wheel 18 with a rotational axis 79 disposed parallel to the incident light. The filter wheel 18 is driven with rotary motion by a motor 80.

A control filter 73 can also be pushed in in front of the filter wheel, as shown in FIG. 1, which corresponds to a predetermined distribution of the components of the waste gases 49 and serves to check the functioning capacity of the device.

Figure 2:
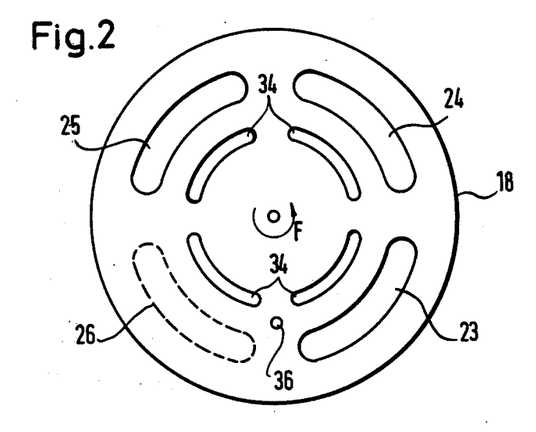
FIG. 2 is a schematic front elevation of the filter wheel used in the device of FIG. 1.

As shown in FIG. 2, the filter wheel 18 comprises as essential elements three filters 23, 24, 25 which are elongated in the circumferential direction and extend in each case over an angle of a little under 90° and which, when a low-pressure mercury-vapour lamp 16 is used, for the source of radiation, consist simply of combinations of tinted glass, the function of which is to pass only one of the three wavelengths 313 nm (filter 23), 435 nm (filter 24) and 546 nm (filter 25), stopping the other two wavelengths in each case.

For the filter 23 a combination of tinted glass UG 11/1 mm and GG 10/1 mm is used conveniently, for the filter 24 a combination of tinted glass BG 3/1 mm and NG 3/1 mm and for the filter 25 a combination of tinted glass OG 515/1 mm and NG 3/1 mm. The designations indicate filters made by the firm of Schott.

Thus according to the invention, by using a selective radiation source 16 for spectral separation it becomes unnecessary to employ expensive and in UV only poorly transparent interference filter, as would be necessary with a wide-band source of radiation. In fact, the highly transparent and cheap combinations of tinted glass are adequate.

As can be seen from FIG. 2, the fourth quadrant of the filter wheel 18 is provided with a dark zone which defines the dark current of the photo-receiver 17 and thereby constitutes a base for measurement of the quantity of light passed by the filters 23, 24, 25.

As shown in FIG. 1, for one revolution of the filter wheel 18, the filters 23, 24, 25 and the dark zone 26 come in succession into the beam path to the photo-receiver 17.

On another circumference of the filter wheel 18 lying further inward are disposed slots 34 which are elongated in the circumferential direction and likewise extend in each case over somewhat less than 90°, each of which is associated with one of the filters or the dark zone 26 respectively. The arrangement in space does not have to be as shown in FIG. 2; it depends upon the arrangement of the light barrier 35 co-operating with the slots 34 along the circumference. The function of the circumferential slots 34 is to generate a clock signal which activates in a suitable way an electronic system, to be described later, while the associated filter, or the dark zone as the case may be, is effective.

Finally, on a third circumference situated between the first and second ones there is provided further a small, round control aperture 36 which co-operates with a further light barrier 37, shown schematically in FIG. 1, and serves to generate a re-setting signal for the master clock and hence to mark the start of the respective cycle.

Instead of the slots 34 and the control aperture 36 it is also possible to provide appropriate reflective marks which co-operate with reflective light barriers. Furthermore, to increase the number of gas components to be measured, the number of filters disposed in the filter wheel 18 may also be increased. In the form represented and with the previously defined filters 23, 24, 25, the filter wheel permits the determination of the smoke components and the gas components $SO_2$ and $NO_2$ in the waste gas 49 in the stack 72.

Thus, on rotation in the direction of the arrow F in FIG. 2, the reflected light beam 78 is split in succession into three wavelengths 546 nm, 435 nm and 313 nm. As will be described in detail below it is important, for simplicity of evaluation, that the gas component $SO_2$ absorbs only at wavelength 313 nm. To exclude cross-sensitivity to the very wide-band absorption of $NO_2$ for the $SO_2$ measurement and in order to be able to indicate the concentration of this component itself, it is measured directly with light of the wavelength 435 nm. The influence of the solid content in the flue gas on measurement at these wavelengths can also be eliminated by formation of a reference signal at wavelength 546 nm as will be described more fully below.

The photo-receiver 17 is preferably a photo-multiplier.

For complete drift compensation there is provided between the light transmitter-receiver 11 and the intake opening 74 in the stack 72 according to the invention a reference reflector 22 which is conveniently constructed as a triple reflector in exactly the same way as the reflector 13. As shown in FIG. 1 the reference reflector 22 is normally disposed beside the beam path. However, it can be moved in the direction of the double arrow $f$ into the position represented by dash-dot lines in FIG. 1 within the beam path so that the light beam 50 incident upon it is reflected back upon itself. The most convenient arrangement is that shown in FIG. 1, that is to say the reference reflector 22 is situated immediately in front of the front objective 20 of the light transmitter-receiver 11 when it is pushed into the beam path. The scavenging air introduced at 71 thus also keeps the reference reflector 22 free from any contamination.

So long as there is no risk, especially of wavelength-dependent drift through the front objective 20 itself, which could be the case in a number of applications, the reference reflector 22 may also be disposed in the interior of the housing 15, that is to say behind the front objective 20.

Figure 3:
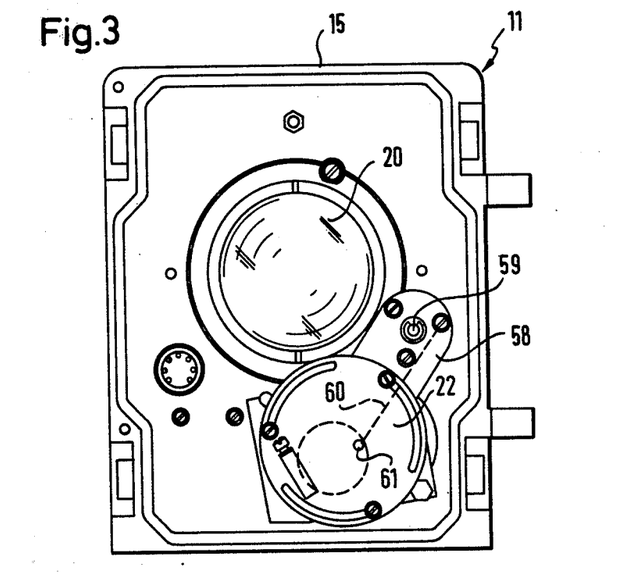
FIG. 3 is the front elevation of a practical embodiment of the light transmitter-receiver of the device shown in FIG. 1.

FIG. 3 shows a front elevation of the light transmitter-receiver 11 with a preferred swinging arrangement for the reference reflector 22. The reference reflector 22 is fastened to a lever arm 58 which is articulated immediately beside the front objective 20 with a rotational axis 59 running parallel to the optical axis. By means of an operating rod 60 which is indicated only schematically, which acts on the lever arm 58 at a short distance from the rotational axis 59, it is possible, by way of a crank 61 driven by a motor — not shown — to exert a torque on the lever arm 58 which causes the reflector 22 to swing into the beam path out of the front objective 20.

Figure 5:
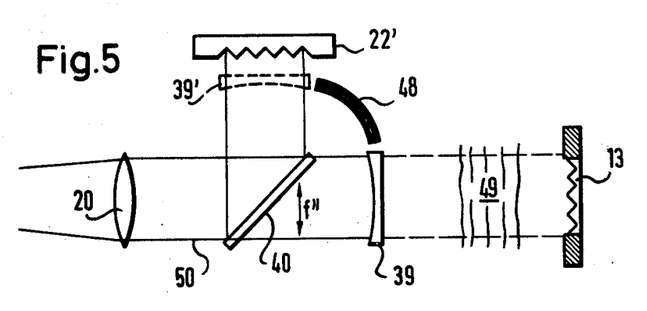
FIG. 5 is a schematic representation of a modified arrangement of the reference reflector which may be used instead of the laterally swingable reference reflector shown in FIGS. 1 and 3.

However, as shown in FIG. 5, a reference reflector 22' running at the side of the beam path and parallel to it may, for example, be fixed and a mirror 40 deflects the light beam 50 towards the reference reflector 22'.

Now, in order to be able to act optionally on the measuring reflector 13 provided at the end of the measured distance 49 and the reference reflector 22', it is possible either to make the deflecting mirror 40 capable of being pushed or swung in the direction of the double arrow $f''$ out of the parallel beam 50 or to construct the mirror 40 as a permanently fixed beam-splitting mirror which thus allows through a part of the incident light beam 50 and deflects another part towards the reference reflector 22'. To ensure that at a certain time only one of the two reflectors 13 or 22' is being acted upon a swivelling diaphragm 39 may be provided which either interrupts the light flow to the retro-reflector 13 in the position shown in solid lines in FIG. 5 or, after swinging round on a swivel path 48, comes into the position 39' shown by broken lines where the light beam can reach the measuring reflector 13 but the light to the reference reflector 22' is interrupted by the swivelling diaphragm

39'. In this form of construction it is particularly advantageous to use as the fixed beam-splitting mirror 40 the beam splitter 77 which is already mounted in the transmitter-receiver housing. The condensing lens 19 would then take the place of the objective 20. An advantage here is the smaller moved mass of the diaphragm 39'. Because of the use of the triple reflector 22' no problems are presented by the adjustment.

Disposed at any point on the part which can move at the change over from measurement to comparison, for example on the reference reflector 22 in FIG. 1, is a contact piece or a cam 29 which co-operates with a contactor 30 in such a way that when the reference reflector 22 is pushed in, a signal relative to this is passed to a master clock 28. In other words the master clock 28 can be aware at all times whether the reference reflector 22, 22' is effective or not.

The following section describes the electronic construction of the device according to the invention.

Disposed on the photo-receiver 17 is a ballast resistor 38, which is made to measure, from which is tapped a voltage which is supplied to a pre-amplifier 21.

The output of the pre-amplifier has a reinforced voltage $U_V$ which is supplied to a channel balancing stage which is of great importance to the invention. The output signal of the pre-amplifier 21 is conducted in parallel to seven amplifiers 41, 42, 43, 44, 45, 46 and 47 with balance. This division of the output signal of the voltage amplifier 21 already presupposes a subsequent channel separation.

The amplifiers 41, 42, 43 are associated with the three wavelengths 313, 435 and 546 nm with the reference reflector 22, 22' swung into the beam path. The amplifiers 44, 45, 46 are associated respectively with one of the three above-named wavelengths with the reference reflector 22 swung out of the beam path, that is to say with an effective measuring reflector 13.

The seventh amplifier 47 with balance belongs to the dark zone 26 of the filter wheel and serves to create a base for measurement at the individual wavelengths with the measuring or the reference reflector in the beam path.

The output signals of the amplifiers 41 to 47 with balance are passed individually to an electronic switch 27 which is controlled by a master clock 28 which picks up control signals $U_R$ from the light barrier 37 and $U_T$ from the light barrier 35 at the filter wheel 18 and also establishes by way of the contactor 30 the effectiveness or non-effectiveness of the reference reflector 22.

A holding circuit 51, 52, 53, 54, 55, 56 is associated with each measuring wavelength both for effective and also for non-effective reference reflector 22 in the switch 27. A seventh holding circuit stores the signal representative of the dark current and conducts it by way of an impedance transducer 32 back to the input of the channel balancing stage 31 in order to form a base.

Scanning by means of the master clock 28 is carried out as follows, reference being made to the pulse diagram in FIG. 4.

Figure 4:
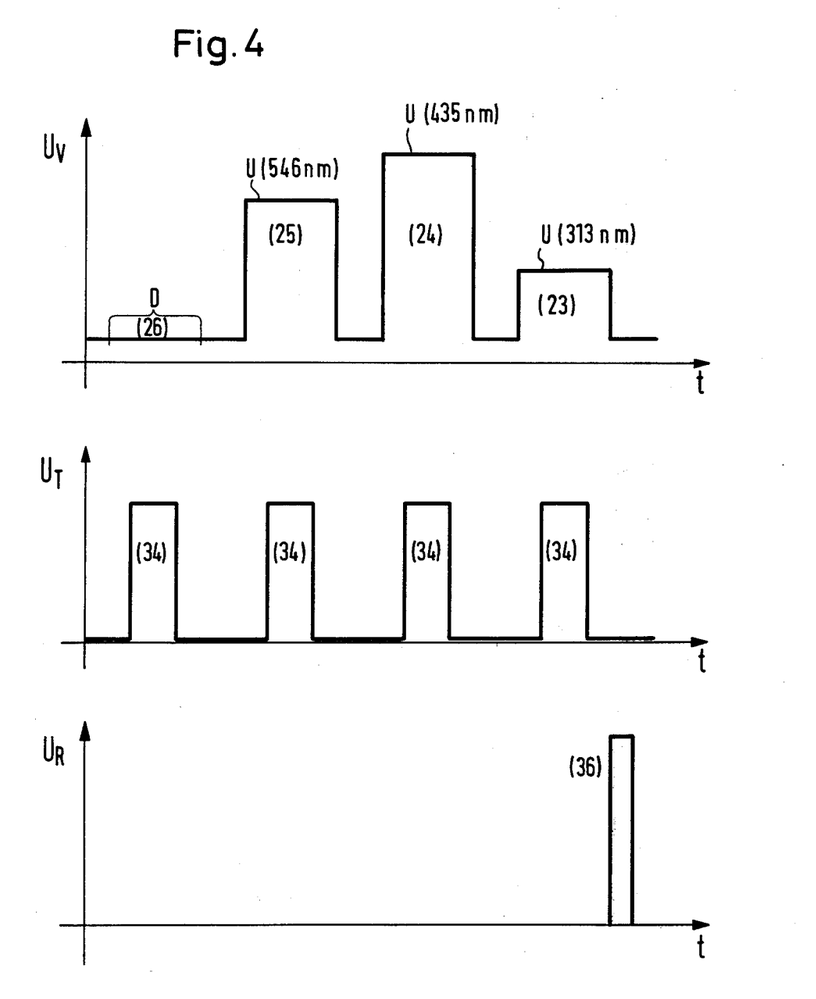
FIG. 4 is a pulse diagram of the photo-receiver controlled by the filter wheel.

At the end of a scanning cycle the control aperture 36 reads out a pulse signal, shown schematically in the bottom diagram in FIG. 4, via the light barrier 37, which signal indicates as signal $U_R$ to the master clock 28 that a new scanning cycle must start.

Now if the dark zone 26 enters the path of the beam to the photo-receiver 17, the holding circuit 57 in the switch 27 is connected to the balancing amplifier 47 so that by way of the impedance transducer 32 a defined base is created for subsequent measuring operation as indicated in the top diagram in FIG. 4 by D.

As soon as the filter 25 enters the beam path the control slot 34 associated therewith, through the release of a second pulse signal $U_T$ to the light barrier 35 (middle diagram in FIG. 4), causes the balancing amplifier 46 to be connected to the holding circuit 56. At the end of the first pulse $U_T$ the balancing amplifier 47 had already been disconnected from the holding circuit 57.

Now, by way of the balancing amplifier 46, the measuring signal produced by reflection at the measuring reflector 13 is stored in the holding circuit 56 at wavelength 546 nm as shown in the top diagram in FIG. 4. As the filters 24 or 23 enter the beam path this cycle is repeated and, as can be seen in the top diagram in FIG. 4, the signals $U_V$ for the wavelengths 435 nm or 313 nm are stored in the holding circuits 55 or 54, respectively.

These cycles are repeated continuously during measuring, the output signals 7, 3, 2 and 1 of the master clock 28 connecting the holding circuits 57, 56, 55 and 54 cyclically with the balancing amplifiers 47, 46, 45, 44.

At intervals of about 10 minutes the reference reflector 22 is pushed into the beam path. The contacts 29, 30 hereby signal to the master clock 28 that the change over from "measuring" to "comparison" has been made. The manner of operation of the master clock 28 consequently changes so that its outputs 7, 6, 5 and 4 connect the holding circuits 57, 53, 52 and 51 cyclically to the balancing amplifiers 47, 43, 42 and 41, respectively. The pulse image is then substantially the same as in FIG. 4 with the sole difference that the heights of the reference pulses associated with the individual wavelengths are different, and indeed higher, by comparison with the "measuring" setting.

Reference figures in brackets show, in the pulse diagram in FIG. 4, to which control apertures or filter zones of the filter wheel in FIG. 2 the individual pulses are assigned.

Thus at the output of the switch 27 there are constantly six signals available at the holding circuits 51 to 56, of which the signals $U_1'$, $U_2'$, and $U_3'$ correspond to the received signals for the individual wavelengths 313, 435 and 546 nm with the reference reflector 22 pushed in, whereas the signals $U_1$, $U_2$ and $U_3$ are representative of the wavelength signals 313, 435 and 546 nm with the measuring reflector 13 operative.

By reason of the balancing possibilities in the amplifiers 41 to 47 it is possible, by carrying out a balancing operation before putting the equipment into use, to bring all the output signals of the holding circuits 51 to 56 to the same level. This applies not only to the individual wavelength signals by comparison with one another but in particular to the output signals which appear when the reference reflector is brought into action, on the one hand, and when the measuring reflector is operative, on the other. In this way, for example, it is also possible to compensate in the simplest and most direct manner differing reflection characteristics of the measuring reflector 13 and the reference reflector 22.

To obtain a coarse balancing between measurement and reference signals it is also possible according to the invention to provide in front of the reflectors rigidly adjustable iris diaphragms (81 in FIG. 6) by means of which both reflectors can be pre-adjusted substantially to the same intensity of reflection.

Evaluation of the signals $U_1'$ to $U_3$ takes place in a computing circuit 33 which will now be described with reference to FIG. 7.

Figure 7:
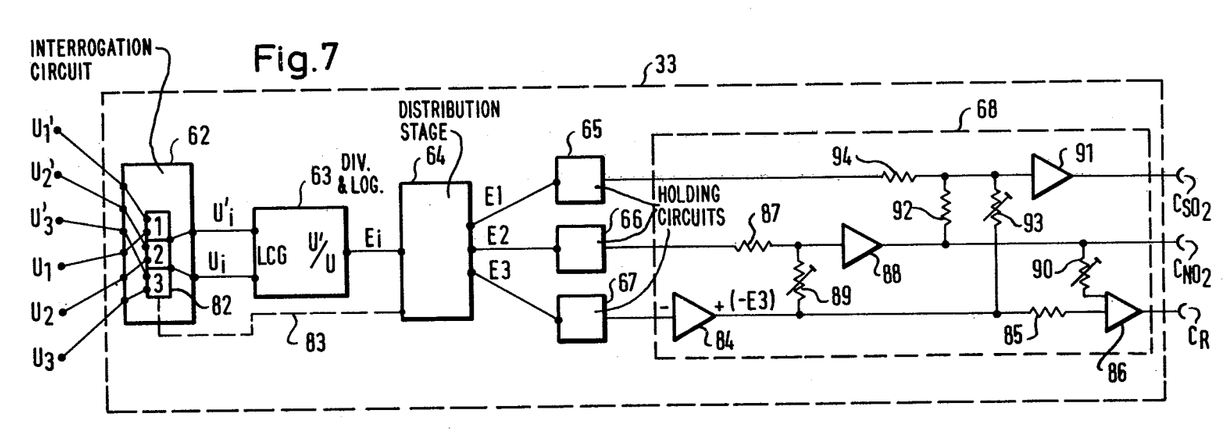
FIG. 7 is a schematic block circuit diagram of the computing circuit used in the device according to the invention.

As shown in FIG. 7 the signals $U_1'$, $U_2'$, $U_3'$, $U_1$, $U_2$ and $U_3$ are passed to an interrogation circuit 62 which contains a switch 82 with an internal master clock by means of which, in the manner illustrated schematically in FIG. 7, the measurement and reference signals $U_1'$ $U_1$ or $U_2'$, $U_2$ or $U_3'$, $U_3$ are passed in succession in pairs to a following division and logarithmic stage 63. There then appears at the output of this stage 63 a signal $E_1$, $E_2$ or $E_3$ depending on which of the three pairs happens to be at the stage 65. These signals $E_i$ are passed to a distribution stage 64 which is also controlled by the internal master clock built into the switch 82 by way of a lead 83, represented schematically. By means of this control the extinction signals $E_1$, $E_2$ and $E_3$ representative of the individual wavelengths are passed to holding circuits 65, 66 or 67 in which they are stored. For the holding circuits it is preferable to use capacitor stores with operational amplifiers.

In another suitable form of construction it would be possible to omit the switch 82 and in three separate division and logarithmic stages 63 to carry out simultaneously a paired processing in each case of the measurement and reference signals $U_1'$, $U_1$, or $U_2'$, $U_2$ or $U_3'$, $U_3$, which would permit a direct further processing of the extinction signals $E_1$, $E_2$ and $E_3$ in the computing stage 68 to be described later without any previous intermediate storage in the holding circuits 65, 66 and 67.

As a result of the formation and processing of the signals picked up by the photo-receiver according to the invention the transmission signals stored in the holding circuits 65, 66 and 67 are totally independent of drift and free from cross-sensitivity. This can be attributed to the fact that all components such as spectral sensitivity of the photo-receiver 17 and spectral emission capacity of the radiation source 16 are contained in the reference signals $U_1'$, $U_2'$, $U_3'$, so that these components which cause the drift drop out when division is performed. Because of this division also, variations in the transmission behaviour of the optical components used show no disturbing manifestations in the measuring process. In particular, ageing phenomena in the lamp and the multiplier no longer affect the measurement. It should be emphasised in particular that comparison is always made with one and the same wavelength, thus excluding disturbances due to different drift at different wavelengths.

The channel balancing in the stage 31 corresponds to an electronic smoothing of the equipment characteristic which is determined substantially by the radiation source 16 and the photo-receiver 17. A remarkable fact is that, besides differences in the reflection behaviour of the measurement and the reference reflector 13, 22, it is also possible to compensate differences of a spectral character individually for the individual wavelengths, which is a considerable simplification of reflector production and adjustment.

Connected on to the holding circuits 65, 66, 67 is a computing stage 68 in which the concentrations of smoke, $SO_2$ and $NO_2$ are calculated from the corrected extinctions values $E_1$, $E_2$ and $E_3$ which are independent of drift.

In measurement of smoke, $SO_2$ and $NO_2$ in the stack 72 and with the use of the wavelengths 313, 435 and 546 nm, the following relationships are obtained for the logarithmic transmission values designated as extinctions $E_i$:

$$E_1 = E_R + {}^1k_{SO_2} = c_{SO_2} \times L + {}^1K_{NO_2} \times c_{NO_2} x \quad (2)$$

$$E_2 = E_R + {}^2k_{NO_2} \times c_{NO_2} \times l \quad (3)$$

$$E_3 = E_R + {}^3k_{NO_2} \times c_{NO_2} \times L \quad (4)$$

In these formulae $E_R$ stands for the smoke extinction, $c$ the concentration of the gas characterised by an index, $k$ the spectral absorption coefficient for the gas concerned at the above-mentioned wavelengths 1, 2 or 3 and L stands for the length of the measured distance. The smoke extinction $E_R$ is related to the dust content as follows:

$$E_R = k_r \times C_r \times L.$$

Allowing for the fact that L and k are constants a gauge for the concentration of $NO_2$ is obtained from the following calculation:

$$f(c_{NO_2}) = E_2 - E_3 = \overline{E_2} = L \times c_{NO_2} ({}^2k_{NO_2} - {}^3k_{NO_2}) \quad (5)$$

A gauge for smoke concentration is obtained from the following calculation:

$$f(c_r) = E_3 - \beta \times \overline{E_2} = \overline{E_3} = E_R \quad (6)$$

where $$\beta = {}^3k/({}^2k - {}^3k) \quad (7)$$

Finally, the concentration of $SO_2$ can be determined from the following formula:

$$f(c_{SO_2}) = E_1 - \gamma \times E_2 - \overline{E_3} = L \times e_{SO_2} \times k_{SO_2} \quad (8)$$

where $$\gamma = ({}^1k - {}^3k)/({}^2k - {}^3k) \quad (9)$$

In order to carry out the above-mentioned calculations the output of the holding circuit 67 is connected via an inverting stage 84 and a resistor 85 to one input of a differentiating stage 86. The output of the holding circuit 66 leads via a resistor 87 to the inverting input of an operational amplifier 88 which at the same time is connected via the regulating resistor 89 to the output of the inverting stage 84.

The output of operational amplifier 88 is also connected via a regulating resistor 90 to the other input of the differentiation stage 86.

The output of the holding circuit 65 is applied via a resistor 94 to the input of the operational amplifier 91 which is also connected via regulating resistors 92 and 93 to the outputs of the inverting stage 84 and the operational amplifier 88. By means of this circuit there appears at the output of the operational amplifier 91 a signal representative of the $SO_2$ concentration, at the output of the operational amplifier 88 a signal representative of the $NO_2$ concentration and at the output of the differentiation stage 86 a signal representative of smoke.

The above values of the coefficients $\beta$ and $\gamma$ are set permanently at the above-defined figures by the ratio of the resistors 92 and 94 or 85 and 90. The balancing which is effected once only is carried out on a section free from test gas and smoke in a simple manner in that with the control filter 73 swung in the concentration values represented thereby are indicated.

Then, as shown in FIG. 1, there can be connected to the three outputs of the computing circuit 33 an indicating instrument 69 which, for example, after voltage-current conversion can take the form of a triple recorder with a respective indicating range 0 to 20 mA in accordance with predetermined concentration ranges so that variations in concentration can be monitored continuously.

As can be seen from FIG. 1, the source of radiation 16, the drives for the filter wheel and reference reflector system, the lamps in the light barriers and also the whole electronic system are supplied from a common power-supply unit.

The arrangement of the reference reflector outside the actual housing for the optical system 15 as shown in FIG. 3 has the advantage that the transmission characteristics of the exit window, which may vary through formation of a deposit, for example, are also included in the drift compensation.

Information on the position of the reference reflector for the master clock can be given by means of a simultaneously rotating cam plate which switches on a relay as soon as the reference reflector 22 is in the beam path.

Figure 6:
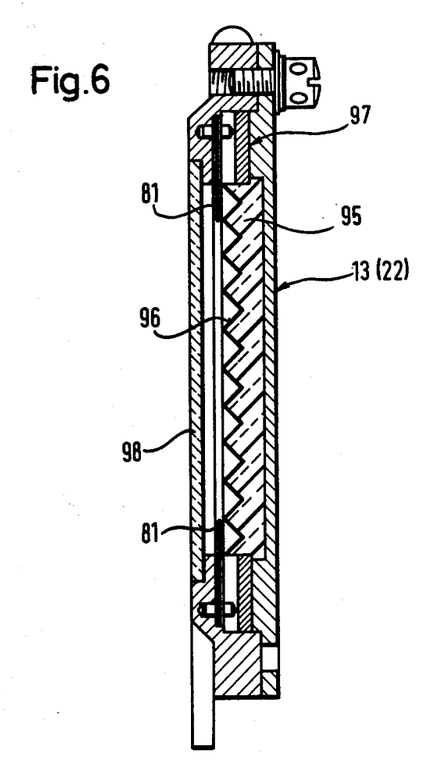
FIG. 6 is a section of the triple reflector used in the device according to the invention.

In FIG. 6 the triple reflector used according to the invention 13 or 22 is of a special construction. Usually, retro-reflectors are constructed on the triple principle in the form of ground or pressed triple mirrors of glass or plastics which the light enters via a plane surface and after total reflection at the internal triple surfaces emerges again deflected in itself with a certain lateral transposition. Triple mirrors of this type are of little use in the invention since the necessary UV-transmission can be obtained hardly at all with pressed plastics triple reflectors and only at great cost with ground quartz glass triple reflectors.

As can be seen from FIG. 6 a less expensive but still very efficient arrangement can be obtained by providing the back of a conventional triple plastics pressing 95 with an aluminum vapour-deposited coating 96 after a preliminary cleaning operation. The surface obtained in this way acts in the same way as a conventional triple reflector but it also reflects in the same way in the ultraviolet range. By means of an additional vapour-deposition with a special UV-permeable protective layer of magnesium fluoride any changes in reflection characteristics due to ageing of the aluminum coating are effectively prevented. The triple reflector 95 thus produced is held in a mount 97 in the manner shown so that the sensitive triple tips are left free. An iris diaphragm 81 disposed in front of the triple reflector 95 can be drawn up to a greater or lesser extent to vary the reflecting surface and fixed in the final position.

It is convenient if the whole arrangement is covered by a window 98 which transmits the ultraviolet.

Figure 8:
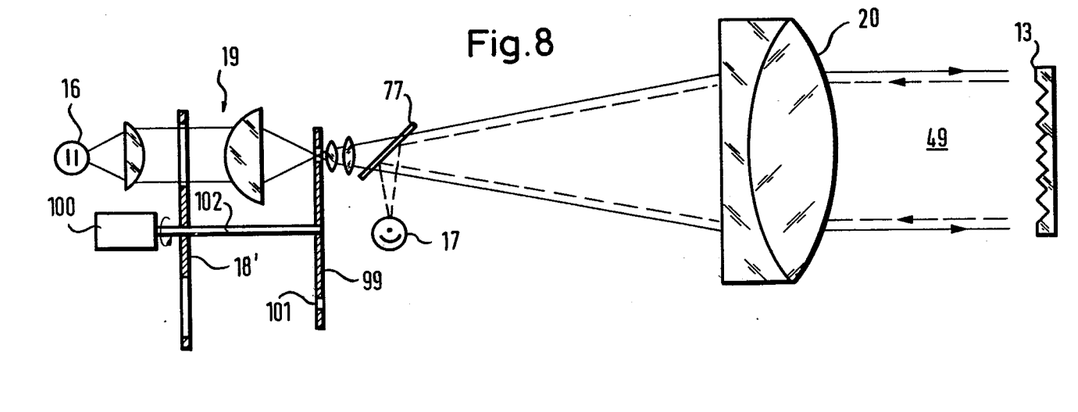
FIG. 8 is a schematic side elevation of a modified part of the device according to the invention shown in FIG. 1 which operates with alternating light.

Under certain conditions it may be favourable to construct the gas analyser with an additional zero scanning of the radiation intensity, as explained below with reference to FIG. 8, showing an alternating light arrangement wherein, in addition to the usual chopper 99 driven by a motor 100, the chopper apertures 101 of which can be brought substantially into the focal point of the condenser 19, a filter wheel 18' is disposed on the same shaft 102. Here the construction of the optical arrangement is such that there is an intermediate imaging at the site of the chopper and thus the diaphragm apertures can be kept small, as a result of which a number of radiation pulses can be obtained for each filter pass. A similar effect can be obtained by pulsing the radiation source and this is possible without any trouble with the low-pressure mercury-vapour lamps which are used. In any case these arrangements need a matched electronics construction with alternating current connection and band-pass filters in their input section.

FIG. 8 is intended to demonstrate that the invention is not restricted to the arrangement of the filter wheel 18 which is represented in FIG. 1. Moreover the above description makes it clear that the method and the device according to the invention can be used to determine more than three gas or smoke components in a mixture of gases, for which at any given time as many radiations of different wavelength required as there are components to be determined.

We claim:

1. Apparatus for non-dispersive optical determination of the concentrations of gas and smoke components in a mixture of gases containing smoke, comprising a light transmitter-receiver for emitting and receiving reflected radiation at one end of a measured distance through the mixture, said light transmitter-receiver being provided with a front objective, a reflector at the other end of the measured distance, a reference reflector arranged to periodically reflect emitted radiation, a photo-receiver in said light transmitter-receiver for receiving radiation reflected by said reference reflector before said radiation enters the mixture, a plurality of wave-length filters, said radiation being passed periodically at successive intervals through at least as many different of said wave-length filters as there are components to be measured during a first predetermined time period, said photo-receiver receiving radiation passed through the mixture, reflected by said reflector, passed through the mixture again and passed periodically at successive intervals through said filters during a second time period, a computer for determining the concentrations of the components in said mixture from electrical signals generated by said photo-receiver and fed to said computer, the computer storing different electrical reference signals for the various test wave-lengths obtained during said first time period and during said second time period and dividing each of the electrical signals influenced by the transmission at the associated wavelength individually by the stored reference signal obtained at the same wavelength, so as to obtain a continuously corrected extinction signal for each wavelength, and transforming the said extinction signals into concentration signals through Beer's Law.

2. Apparatus according to claim 1, wherein the reference reflector can be swung into the beam path between the light transmitter-receiver and the measured distance.

3. Apparatus according to claim 1 wherein the reference reflector is fastened to a lever arm for moving the same to a position immediately adjacent the front objective of the light transmitter-receiver.

4. Apparatus according to claim 3, wherein at a short distance from the fulcrum of the lever arm there is situated an operating rod which can be driven in both directions by a motor through a crank.

5. Apparatus according to claim 1, wherein each reflector is a retroreflector.

6. Apparatus according to claim 5, wherein the retroreflector is a vapour-deposited aluminium coating on a plastics triple pressing.

7. Apparatus according to claim 5, wherein at least the reflector disposed at the end of the measured distance is irradiated on all sides by a light beam emitted by said light transmitter-receiver.

8. Apparatus according to claim 1, wherein an auto-collimation beam path is employed.

9. Apparatus according to claim 1, wherein a low-pressure mercury-vapour lamp is employed as a light source in said light transmitter-receiver.

10. Apparatus according to claim 1, wherein wavelength selection is effected by a filter wheel which has, on a first circumference, filters which successively receive light in the form of reflected radiation.

11. Apparatus according to claim 1, wherein a low-pressure mercury-vapour lamp is employed as a light source in said light transmitter-receiver and the filters consist of combinations of tinted glass.

12. Apparatus according to claim 10, wherein in the sequence of said filters there is also provided a dark zone on said first circumference of said filter wheel.

13. Apparatus according to claim 12, wherein there is further provided a master clock, and on a second circumference of said filter wheel there are provided control slots co-operating with a light barrier and said master clock, each of which slots being associated with one of said filters and said dark zone.

14. Apparatus according to claim 13 wherein on a third circumference of said filter wheel there is provided a control aperture cooperating with a second light barrier to generate a re-setting signal for said master clock.

15. Apparatus according to claim 1, wherein the photo-receiver is connected through a pre-amplifier to a channel balancing stage which has a balancing amplifier for measuring each wavelength.

16. Apparatus according to claim 15, wherein a balancing amplifier is also provided in the channel balancing stage for dark zone signals.

17. Apparatus according to claim 15, wherein an electronic switch controlled by a master clock is connected to the channel balancing stage which switch stores wavelength measuring and reference signals received by said photo-receiver, and also where applicable dark zone signals, individually in holding circuits.

18. Apparatus according to claim 17, wherein a computing circuit is connected to said electronic switch which circuit interrogates in pairs and divides by one another the measuring and reference signals belonging to the same wavelength.

19. Apparatus according to claim 18, wherein logarithms are taken in the computing circuit of the signals which are divided by one another.

20. Apparatus according to claim 19, wherein the logarithm signals representing the extinctions are stored in holding circuits.

21. Apparatus according to claim 20, wherein a computing stage is connected to the holding circuits, which stage forms the concentration signals from the logarithm signals.

22. Apparatus according to claim 1, wherein pre-set iris diaphragms are disposed on at least one of said measuring reflector and reference reflector.

23. Apparatus according to claim 1, wherein operations are carried out with alternating light.

24. Apparatus according to claim 23, wherein a chopper and a filter wheel are disposed on the same shaft.

25. Apparatus according to claim 15, wherein the channel balancing stage has two balancing amplifiers for each measuring wavelength.

26. Apparatus according to claim 1, wherein wavelength selection is effected by a filter wheel which has, on a first circumference, filters which successively receive light in the form of reflected radiation, said sequence including a dark zone; on a second circumference, control slots so-operating with a light barrier and a master clock, each of which slots is associated with one of said filters and dark zone; and on a third circumference, a control aperture co-operating with a second light barrier and the master clock.

27. Apparatus according to claim 1, wherein the photo-receiver is connected through a pre-amplifier to a channel balancing stage which has a balancing amplifier for each measuring wavelength and a balancing amplifier in the channel balancing stage for dark zone signals, an electronic switch controlled by a master clock connected to the channel balancing stage which switch stores wavelength measuring and reference signals received by said photo-receiver and also where applicable the dark zone signals, individually in holding circuits; a computing circuit being connected to said electronic switch which circuit interrogates in pairs and divides by one another the measuring and reference signals belonging to the same wavelength.

28. Apparatus according to claim 27, wherein logarithms are taken in the computing circuit of the signals which are divided by one another and the logarithm signals representing the extinctions are stored in holding circuits, a computing stage being connected to the holding circuits, which stage forms the concentration signals from the logarithm signals.

29. Apparatus according to claim 26, wherein each reflector is an aluminium coated retro-reflector and at least said reflector disposed at the end of the measured distance is irradiated on all sides by a light beam, emitted by said light transmitter-receiver, the path of said beam being autocollimated.

* * * * *